(12) United States Patent
Green

(10) Patent No.: US 7,257,907 B2
(45) Date of Patent: Aug. 21, 2007

(54) INSTANT CUSTOM MOLDABLE INSOLE

(76) Inventor: David Green, 23 Lesmill Rd., Suite 401, New York, Ontario (CA) M3B 3P6

( * ) Notice: Subject to any disclaimer, the term of this patent is extended or adjusted under 35 U.S.C. 154(b) by 65 days.

(21) Appl. No.: 11/186,355

(22) Filed: Jul. 20, 2005

(65) Prior Publication Data

US 2006/0016103 A1    Jan. 26, 2006

Related U.S. Application Data

(60) Provisional application No. 60/521,917, filed on Jul. 21, 2004.

(51) Int. Cl.
*A43B 7/14* (2006.01)
*A43B 13/38* (2006.01)

(52) U.S. Cl. .............. 36/93; 36/44; 36/71; 36/154; 12/146 M

(58) Field of Classification Search ............. 36/91, 36/93, 43, 44, 154, 153, 88; 12/146 B, 146 M, 12/142 N
See application file for complete search history.

(56) References Cited

U.S. PATENT DOCUMENTS

| | | | | |
|---|---|---|---|---|
| 2,366,323 A * | 1/1945 | Fried | ............................ | 36/154 |
| 4,211,019 A * | 7/1980 | McCafferty | ..................... | 36/43 |
| 4,385,024 A * | 5/1983 | Tansill | ......................... | 264/223 |
| 5,042,100 A * | 8/1991 | Bar et al. | .................. | 12/142 N |
| 5,083,910 A * | 1/1992 | Abshire et al. | ................ | 425/2 |
| 6,098,315 A * | 8/2000 | Hoffmann, III | ................ | 36/91 |

* cited by examiner

*Primary Examiner*—Jila M Mohandesi
(74) *Attorney, Agent, or Firm*—White-Welker & Welker, LLC

(57) ABSTRACT

A custom moldable insole comprising a first chamber containing a silicone base and a second chamber containing a catalyst. Both fluids are forced to pass though a shared static mixing channel where they will thoroughly mix and flow into a third chamber. The third chamber is a continuation of the mixer that opens up into a bag to hold the silicone as it flows to the arch and metatarsal areas of the foot in the upper layer of the insole. Within a few minutes as the user stands wearing the shoe the silicone cures to the shape of the bottom of the wearers foot providing increase support and comfort.

15 Claims, 10 Drawing Sheets

INSTANT CUSTOM MOLDABLE INSOLE

CROSS REFERENCE TO RELATED APPLICATIONS

This application claims priority from U.S. Provisional Patent Application Ser. No. 60/521,917, entitled "Custom Moldable Insole", filed on Jul. 21, 2004.

TECHNICAL FIELD OF THE INVENTION

The present invention relates generally to shoe inserts. More specifically the present invention relates to instant moldable orthotic insoles.

BACKGROUND OF THE INVENTION

Various shoe inserts are used to provide comfort, support, cushioning, and/or stability to the foot. For individuals suffering from serious podiatric conditions, such as abnormal walking patterns, custom orthotics prescribed by a physician are necessary. One drawback of custom orthotics is that they are generally expensive and time-consuming to fabricate. For other individuals, off-the-shelf, pre-formed, shoe inserts provide sufficient support and comfort.

An intermediary option where an off-the-shelf insert that is conformed to an individual's foot either at the time of purchase of the insert or thereafter, without the participation of a physician has been taught in various manners and is generally known in the prior art. Such instant moldable orthotic insoles need no mold, lab, weeks of waiting and are available at a greatly reduced cost.

U.S. Pat. Nos. 5,203,793, 5,101,580, and 4,674,206 to Lynden, teach several sole insert devices containing conformable material substantially comprising fluid matter which forms a resilient material substantially comprising solid matter after a working time. In more specific examples, Lynden teaches a personalized insert containing a resilient material, which comprises at least two compartments separated by a restraining pin or one or more membranes, which compartments separate two reagents that, when mixed, catalyze to form an insert resilient material. Removal of restraining pin(s), and/or the rupture of the membranes isolating the reagents, permits fluid communication and proper mixing of the reagents to form the resilient material. The resilient material then sets in conformance with the wearer's foot when the insert is secured within an article of footwear.

The sole insert devices taught by Lynden have the two reagents separated from each other using a pin dividing a bag. This is a very ineffective means to mix the silicone thoroughly and quickly.

To overcome the shortcomings in the Lynden devices, the present invention uses a static mixer with the strong force of the weight of the wearer pushing it though the mixer. This allows the use of a higher viscosity silicone, which helps to fit the wearers fit without requiring the user to sit still for more than a few minutes.

A common problem in the prior art is the use of lower viscosity fluids are likely to escape into areas at the edge of the bag that make it much harder to receive a complete mixing and therefore do not provide even support throughout the insole. The present invention overcomes this shortcoming by using a static mixing device built into the arch of the shoe and limiting the areas to which the silicone can flow. The advantage is that the silicone will completely mix before even entering the area under the arch and therefore cure very quickly while the user can still stand still. This can only be achieved with high viscosity silicone because low viscosity silicones will otherwise return to a neutral position until the silicone is more advanced in it's curing.

Still another disadvantage of Lynden's system is that the bag lies flat under the insole providing very little support other than that shaped by the silicone.

It is therefore an objective of the present invention to build the silicone injection system into an already supportive insole so that the silicone will provide only the amount needed for customization above the minimum that most wearer's will likely need. This is achieved by housing the static mixer in the arch of the sole that is already providing some support while hiding the mixer.

Yet another shortcoming in Lynden's system is its complicated use. A user needs to access the insole outside of the shoe, remove the pin and while the fluid is beginning to cure, put it in the shoe and stand in the right position on both feet. This process is confusing and difficult for the average user. It is therefore an objective of the present invention to teach a device that is less complex in its use.

The present invention is designed without the need for a pin, tab or key of any sort to initiate activation. To use, a user simply stands in the shoe and the fluid is injected and mixed. This insures that the exact timing of the curing and shaping of the silicone is always the same because no delay is possible between activating the curing and standing on the insole.

U.S. Pat. No. 5,958,546 to Mardix, et al., teaches a method for producing a custom insole including the steps of providing a preformed insole precursor, the precursor being constructed of a solid material which is storable in an unreformed state and which is compressible to a deformed configuration under pressure substantially at room temperature and which retains the deformed configuration after removal of the pressure, and pressing the foot on the insole precursor, thereby compressing the insole precursor and forming an insole with a configuration in accordance with the configuration of the foot.

U.S. Pat. Nos. 5,042,100 and 5,095,570 to Bar et al. teaches techniques for producing an insole for a foot, including defining a flexible insole housing in which is disposed a deformable material impregnated with an uncured resin, activating the resin for initiating curing thereof, locating the foot on the insole housing and allowing the resin to harden and to therefore preserve the configuration defined by the bottom of the foot. Bar's device is impractical as an off the shelf product. It still has the same problems as the Lynden Devices, problems of even mixing and control of timing from the point of being put on a user's foot.

U.S. Pat. Nos. 4,385,024, 4,128,95 to Tansill, teach a moldable article, such as an insole, which comprises a formable material that is a moldable polymeric or prepolymeric substance that can be cured to a form stable state and a curing agent, in close proximity to the curable substance but isolated there from, in a frangible container. The container containing the curing agent is initially flexible and is rendered frangible by treatment. In use, the frangible container is ruptured to release the curing agent, and the moldable article, in a first configuration, can be shaped to a second configuration in which it is maintained until the formable material is cured sufficiently for it to be form-stable in the second configuration.

Tansill suffers from the same disadvantages as Lynden since no static mixer. In Tansill's device, a user first needs to rupture the bag containing the catalyst that then needs to be shaken up resulting in a delay. Although with better mixing then Lynden, Tansill's device can't be compare to an internal static mixer and the pressure of someone standing on the heel to push the fluid through at equal ratio.

U.S. Pat. No. 6,098,315 to Hoffmann, III, teaches an insert for a shoe comprising a pouch having a moldable, thixotropic material and a shell having a catalyst. The shell is capable of being ruptured by massaging the pouch to allow the catalyst to be released from the shell and mixed with the material. In use, the pouch is massaged to mix the catalyst and moldable material and is then placed in a shoe. The user places a foot in the shoe and applies a lightweight to the foot so that the pouch assumes the shape of the foot bottom and fills that space between the foot and the shoe. The foot is then removed to allow the material to cure.

The device of Hoffmann requires puncturing, massaging, and manual injection of catalyst, massaging again to mix properly, insertion into a user's shoe and then removal from shoe in order to cure. The process is much too slow and risky due to its complexity, timing of wearing the insole from the point of mixing the catalysts, and risk of shape changing at the beginning of curing process. It is therefore an objective of the present invention to provide an apparatus that is quick and simple to use.

U.S. Pat. No. 5,083,910 to Abshire, et al., teaches a custom fitted insole assembly for use in a shoe directly under a wearer's foot. The assembly includes a heel-cupping and arch-supporting base component custom contoured to fit the heel and arch of the wearer's foot, a heel stabilizing component attached to an underside heel region of the base component, and a shock-absorbing top sheet component sized to underlie the bottom of the wearer's foot and at its rear half to overlie and conform to the contour of the base component.

SUMMARY OF THE INVENTION

A custom moldable insole comprising a first chamber containing a silicone base and a second chamber containing a catalyst. Both fluids are forced to pass though a shared channel where they will thoroughly mix and flow into a third chamber. The third chamber is a continuation of the mixer that opens up into a bag to hold the silicone as it flows to the arch and metatarsal areas of the foot in the upper layer of the insole. Within a few minutes as the user stands wearing the shoe the silicone cures to the shape of the bottom of the wearers foot providing increase support and comfort.

DETAILED DESCRIPTION OF THE INVENTION

In the following detailed description of the invention of exemplary embodiments of the invention, reference is made to the accompanying drawings (where like numbers represent like elements), which form a part hereof, and in which is shown by way of illustration specific exemplary embodiments in which the invention may be practiced. These embodiments are described in sufficient detail to enable those skilled in the art to practice the invention, but other embodiments may be utilized and logical, mechanical, electrical, and other changes may be made without departing from the scope of the present invention. The following detailed description is therefore, not to be taken in a limiting sense, and the scope of the present invention is defined only by the appended claims.

In the following description, numerous specific details are set forth to provide a thorough understanding of the invention. However, it is understood that the invention may be practiced without these specific details. In other instances, well-known structures and techniques known to one of ordinary skill in the art have not been shown in detail in order not to obscure the invention.

Figure 1:
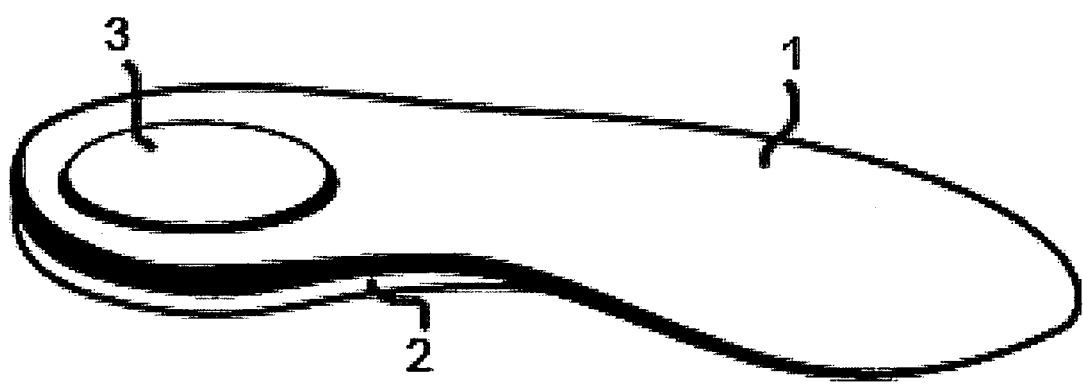
FIG. 1 is a schematic illustration of a custom moldable insole, in accordance with the shell embodiment of the present invention.

Now referring to FIG. 1 a "shell" embodiment of the insole required is housed within a stable three-layer insole using a shell 2, top insole 1 and middle bag and mixer. It looks much like most insoles except for its bulge in the heel 3 which houses the unmixed silicone before used by the wearer.

Figure 2:
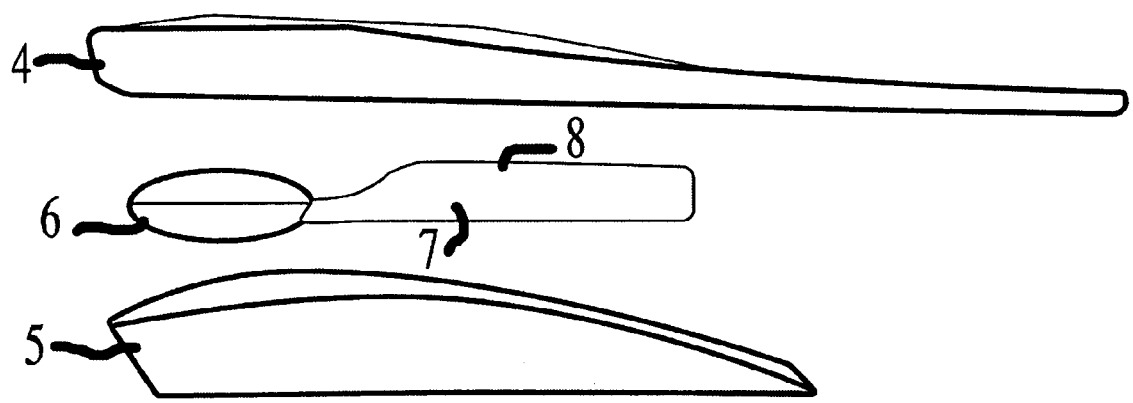
FIG. 2 is a schematic cross-sectional view of the insole of FIG. 1 in accordance with an embodiment of the present invention showing each of the three layers before sealing them together into one insole.

The middle layer, as illustrated in FIG. 2, is a one-piece bag and mixer 4 that locks into position within the bottom shell 5 and then seals together with the top insole 6.

Figure 3:
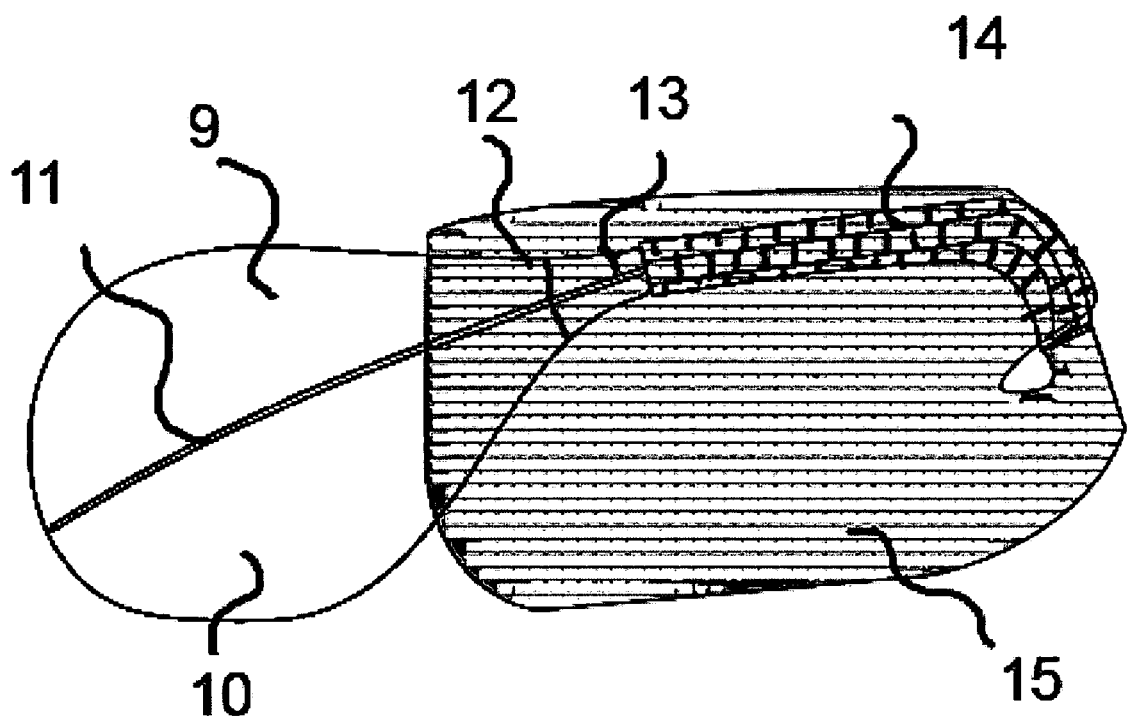
FIG. 3 is a schematic view of the bag and mixer inside an insole.

The bag and mixer, as illustrated in FIG. 3, embodies a two chamber bag containing a 1:1 silicone solution with a first chamber 9 and a second chamber 10 separated by a divider 11 which is part of the same piece of soft plastic. A thin plastic membrane 12 holds the unmixed silicone in both the first chamber 9 and second chamber 10 until it is time to inject it though the attached mixing tube 14 where the silicone is thoroughly mixed by being forced through a number of small holes and passageways. To minimize any risk of premature leaking of the silicone into the mixing tube, the divider 11 between the first chamber 9 and second chamber 10 is extended 13 beyond the thin membrane 12 in order keep any escaped silicone from mixing should they leak into the mixing tube. Once the silicone has been mixed it continues to travel to a flat chamber 15 at end of the mixing tube towards the toe of the insole.

Figure 4:
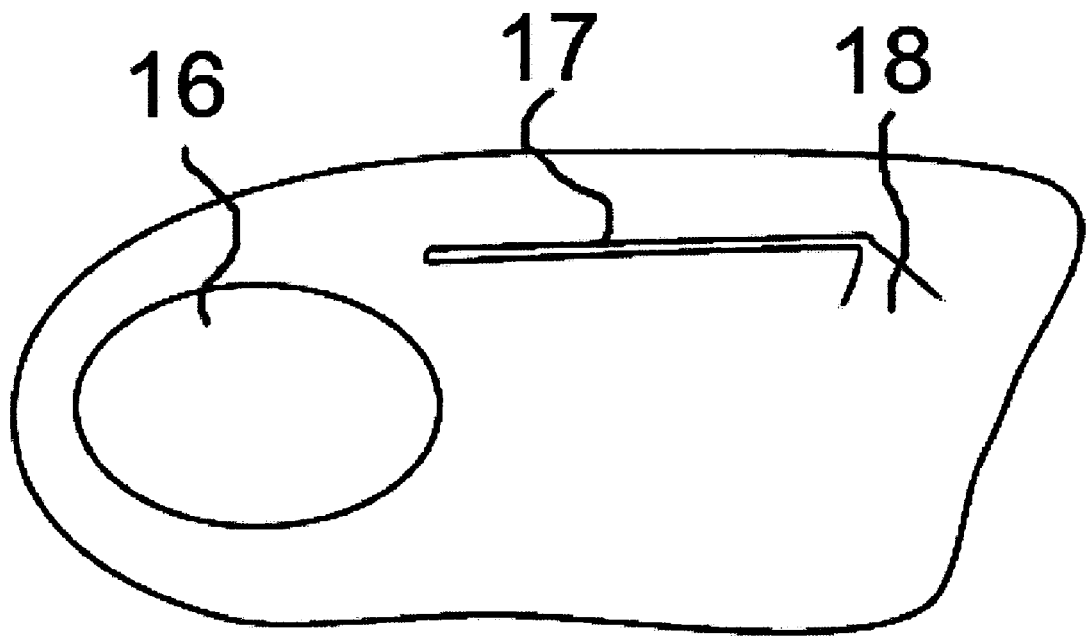
FIG. 4 is a top view of the plastic shell used as the bottom layer of an insole.

Now referring to FIG. 4, the plastic shell at the bottom of the insole consists of a hole 16 in the heel to help house the two-chamber bag containing the unmixed silicone. There is channel in the shell designed to lock the mixing tube into position under the arch of shell. FIG. 4, being a top view of the shell, shows just the thin slot 17 over the top of the channel. By bending the shell, the channel opens in order to place the mixing bag and tube into position within the shell during manufacturing. The end of the channel bends towards the middle of the insole where the mixed silicone enters the third chamber 18.

Figure 5:
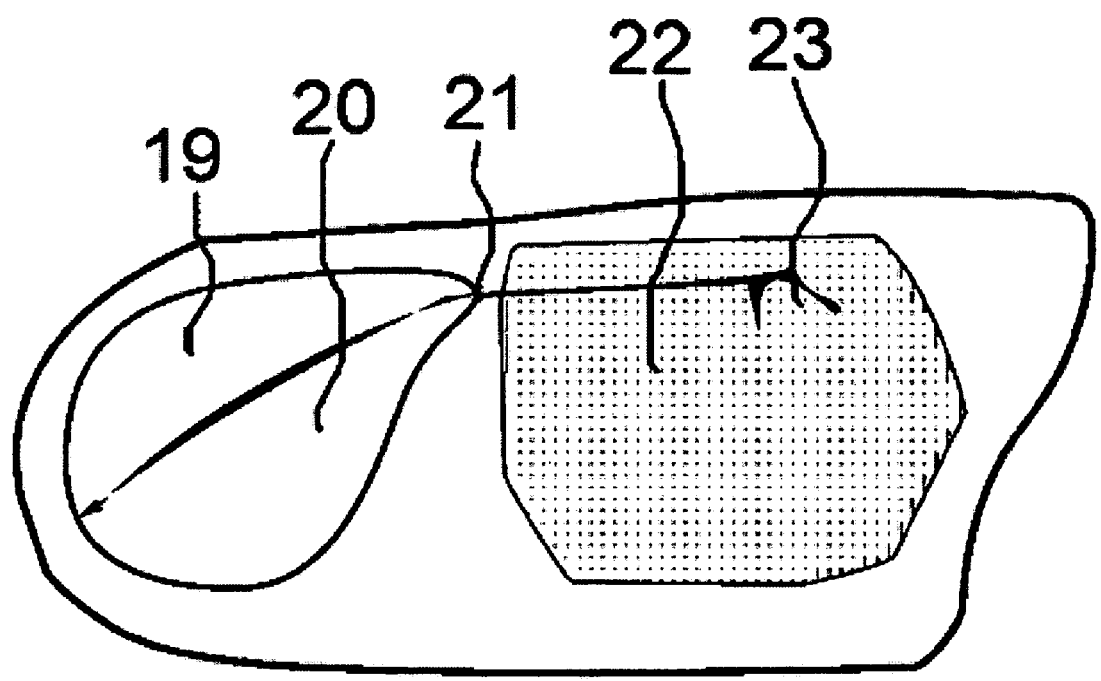
FIG. 5 is a schematic illustration the bag and mixer locked in its proper position within the shell of an insole.

Now referring to FIG. 5, the plastic bag/mixer sits in the hole 16 in the heel of the shell resting the two-chamber bag containing silicone A 19 and silicone B 20 in the heel. The mixing tube is firmly locked in the channel 21 in the shell. The channel and the tube bend 23 towards the center of the insole where the silicone is released into the third chamber bag 22.

Figure 6:
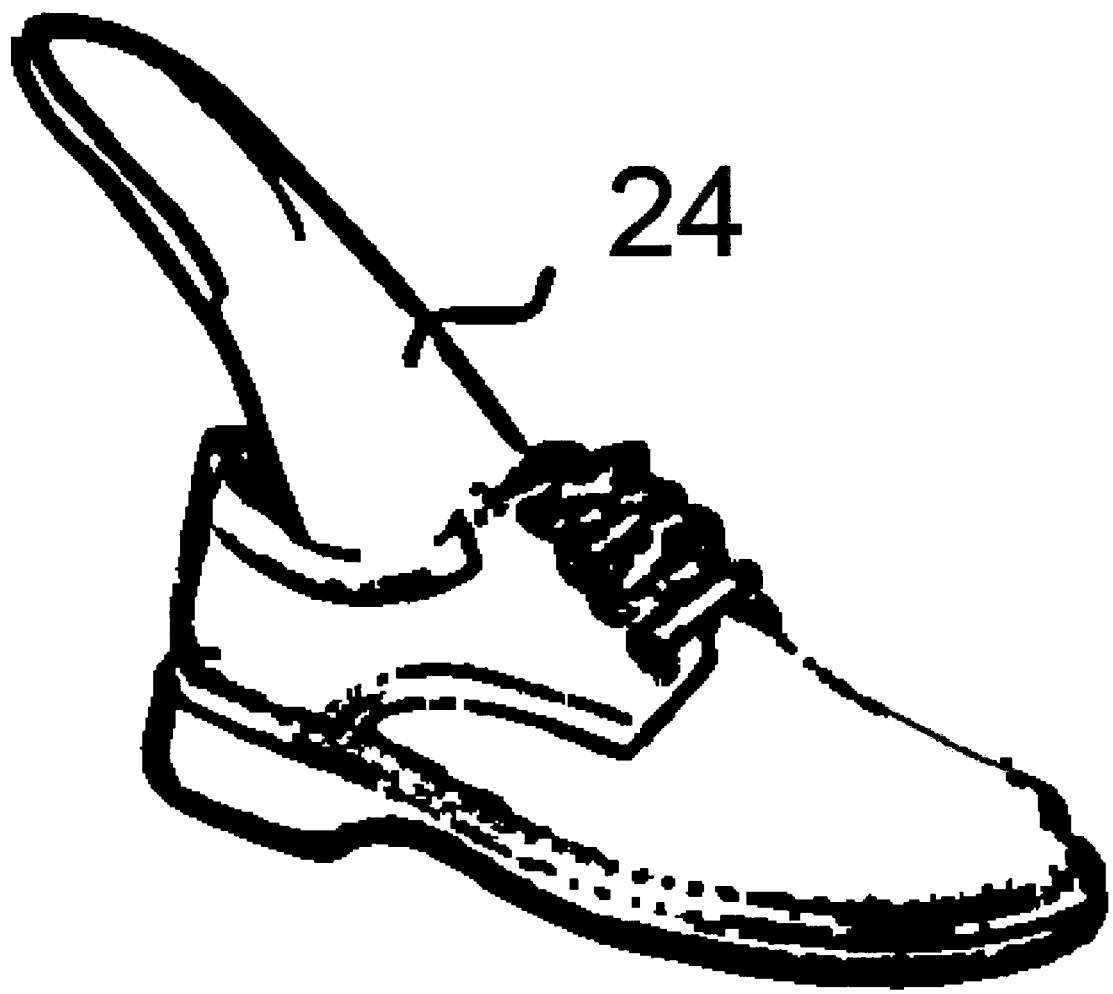
FIG. 6 is an illustration of how an insole is placed into a typical shoe before the wearer stands on it for use.

FIG. 6 shows how the complete insole 24 is placed into the wearers shoe ready to be used without any need to remove any tabs or locks.

Figure 7:
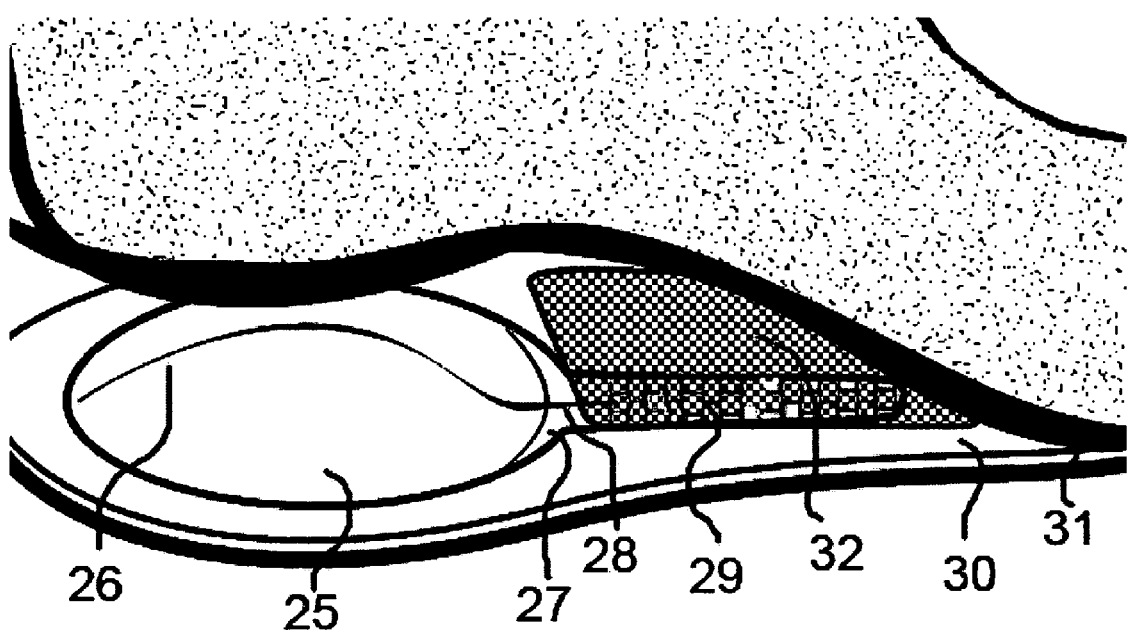
FIG. 7 is a schematic cross-sectional view of the mixing bag in its position in relation to the wearer's foot as the wearer stands on the insole to inject the silicone through the mixer.

FIG. 7 illustrates how a user steps into the insole. When their heel is lowered the weight of the wearer is placed primarily on the heel of the insole and onto the two-chamber bag 25 containing the two-part silicone. The membrane 27 keeping the silicone in the two-chamber bag 25 breaks from the pressure and the silicone from both sides of the bag divider 26 is quickly injected through the mixing tube 29. On the other end of the tube is a flat plastic bag 32 shaped to cover all the areas of the insole that might need additional support. The top insole 31 is made of a very flexible material so to allow as much of the shape of the wearers foot to shape the silicone as it cures.

Figure 8:
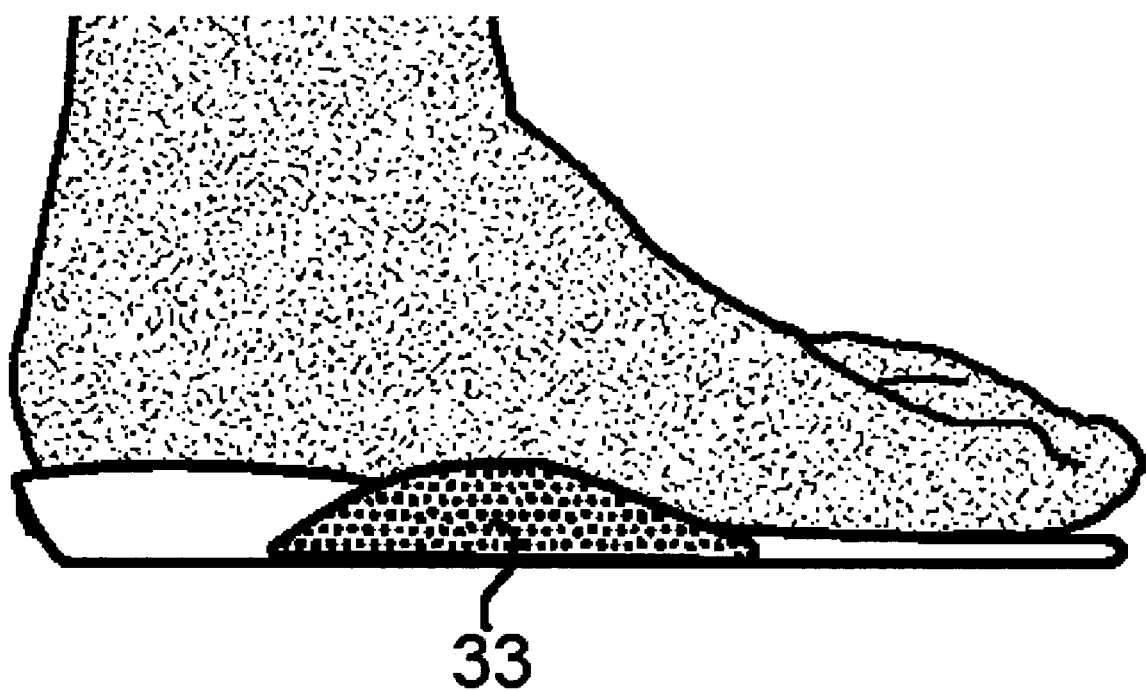
FIG. 8 is a schematic cross-sectional view of the mixing bag in it's position in relation to the wearer's foot after the wearer has stepped on the insole causing the silicone to be injected through the mixer.

Now referring to FIG. 8, within a few minutes of standing on the insole, the silicone in the third chamber bag 33 will flow to the areas in need of support such as the arch and metatarsal.

Figure 9:
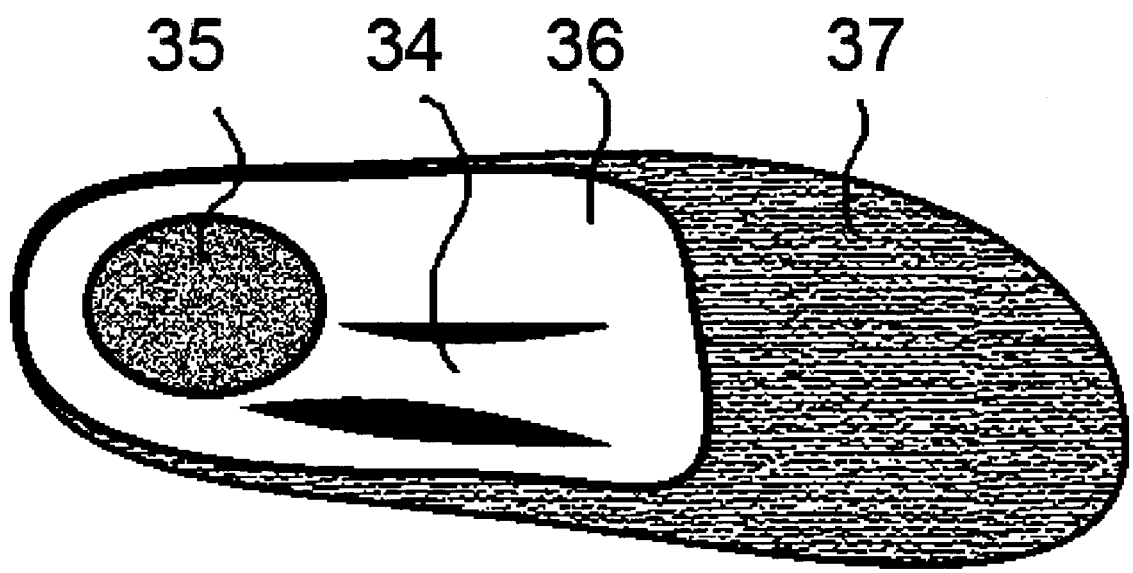
FIG. 9 is a schematic view of the bottom of an insole.

FIG. 9 illustrates the bottom of the plastic shell that has a hole 35 in it to allow the unmixed silicone in the bag in the heel to fit easily by using a little space from both above and bellow the level of the plastic shell 36. The plastic shell is shaped with a channel 34 to hold the mixing tube/bag. The plastic shell is sealed to the bottom of the top insole 37.

Figure 10:
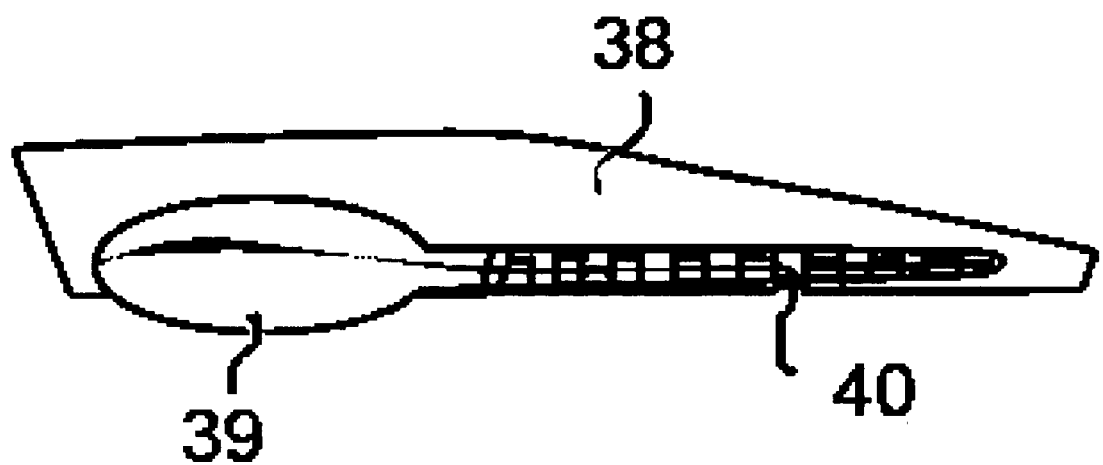
FIG. 10 is a schematic cross-sectional view of the mixing bag positioned over the hole in the heel of the shell of an insole.

FIG. 10 is a side view illustration of the bag 39 and mixer 40 sitting within the hole and channel in the shell.

The method of use for the instant moldable orthotic insole of the present invention is as follows. First a plastic bag 2 parts containing silicone 1:1 ratio of A and B housed within the outer bag that forms into the mixing tube and then the mixed silicone receiving bag. A thin membrane breakable from pressure of 100 lbs or more only when stood on by user, prevents premature activation. This also avoids having to use tabs, strings, external injectors or application of heat to prepare the insole for use.

Once the inner bags break, the silicone flows into the chamber containing the static mixer that is built into the tube leading to the front of the insole. The static mixer can be spiral, or any other configuration allowing the providing of the 2 part silicone solution meet and mix several times before exiting the mixing tube. The mixing tube opens up into bag the mixed silicone-receiving bag where the mixed silicone spreads under the top layer of the insole to create exact mold of the user's foot. The bag is fairly flat with its circumference shaped to allow silicone flow to the arch, metatarsal and other areas of the foot that may need extra support.

The silicone hardens within a few minutes by using a medium viscosity 1:1 silicone solution. The silicone flows easily under pressure through the mixer while being thick enough to help speed up the curing process. Hardened silicone is not stiff like insoles on the market since they are shaped to the user's feet while in their shoes. This overcomes the need for the insoles to be sitting above the shape of the shoe. This creates a much more comfortable orthotic without sacrificing on the support provided.

The insole of the present invention is designed to house a full silicone injection system within the shape of a typical insole by using a plastic shell on the bottom with a cavity to hold the unmixed silicone bags, mixing tube and mixed silicone receiving bag. The mixing tube containing the static mixer is the thickest part of the injection system and is therefore housed in the arch of the shell. The injection system clamps securely into the shell of the insole so it will not move at all before or after use. The injection system fits into channel and cavities in the shell in a position leaving a smooth surface on top. This enables the silicone to easily flow to all its needed areas once it has been injected into the receiving bag.

The heel of the shell has a hole in it to leave room for the bags containing unmixed silicone without pushing too much only to the top of the insole which would create an unwanted stretching on the top layer of the insole. The hole is the right size to allow the unmixed silicone bags to protrude equally out the bottom and the top of the insole without having to stretch either one too much.

In addition, other areas of art may benefit from this method and adjustments to the design are anticipated. Thus, the scope of the invention should be determined by the appended claims and their legal equivalents, rather than by the examples given.

The invention claimed is:

1. An insole apparatus comprising:
   a top layer of an insole;
   a plastic bag disposed beneath the top layer of the insole, the plastic bag including a first and second compartment,
   a first liquid compound contained within said first compartment; and
   a second liquid compound contained within said second compartment;
   a mixing channel on one end connected to the first and second compartments of the plastic bag, said end containing a thin breakable membrane and connected on an opposing end to a mixing bag; and
   the mixing channel having a spiral shape allowing the first and second liquid compounds to meet and mix several times as they flow from the first and second compartments before exiting the mixing channel and into the mixing bag.

2. The apparatus of claim 1 wherein upon the breaking of the thin breakable membrane; the two liquid compounds flow into a chamber containing a static mixer that is built into the mixing channel leading to the front of the insole; said mixing channel opens up into the mixing bag where the first and second liquid compounds spread.

3. The apparatus of claim 2 wherein the mixing bag is flat with its circumference shaped to allow the first and second liquid compounds to spread to the region of the mixing bag corresponding with the arch, metatarsal and other areas of a foot.

4. The apparatus of claim 1 wherein a shell cavity accommodates the plastic bag, mixing channel, and mixing bag.

5. The apparatus of claim 1 wherein the mixing channel is housed beneath the arch area of the foot.

6. The apparatus of claim 4 wherein the plastic bag has a smooth top exterior surface.

7. The apparatus of claim 1 wherein the mixing compound will meet and mix several times as they flow from the first and second compartments before exiting the mixing channel and into the mixing bag.

8. The apparatus of claim 1 wherein the mixing channel is comprised of a round, narrow channel containing therein a plurality of spiral mixing elements to repeatedly mix the liquid compounds that flow through the mixing channel.

9. A method for creating custom insoles comprising the steps of:
   selecting an insole having a top and bottom part, said insole's bottom part comprised of a first chamber filled with a first substance and a second chamber filled with a second substance;
   placing a mixing channel beneath the bottom part of the insole leading to a third chamber located under the arch area of the foot;
   providing a key for the mixing channel at its entrance from said first and second chambers; and
   releasing said key so as to transfer fluid from the first and second chambers to flow together into said third chamber; and
   allowing said insole to cure.

10. The method for creating custom insoles of claim 9 comprising the additional step of providing a means for placing a pressure evenly upon both the first and second chambers.

11. The method for creating custom insoles of claim 10 comprising the additional steps of:
    positioning the first and second chambers at the region of the insole corresponding with the heel of a foot,
    providing said pressure means with a firm flap of rubber that pushes evenly upon both the first and second chambers forcing the substances to flow into the mixing channel and then into the third chamber to cure.

12. The method for creating custom insoles the insole apparatus of claim 10 comprising the additional steps of:
    positioning said first and second chambers in the region of the insole corresponding with the heel of a foot,
    placing the insole into a shoe, and
    standing in neutral position as the mixture cures to the shape of the wearer's foot.

13. The method for creating custom insoles of claim 10 comprising the additional steps of:
    providing the first and second chambers with a catalyst and a base;
    positioning the first and second chambers at the region of the insole corresponding with the heel of a foot;
    positioning a stiff flap of rubber or plastic on the bottom of the insole, above the first and second chambers containing the catalyst and base, with the flap opening leading to the mixing channel;
    where a pressure applied by a wearer forces the flap to push the catalyst and base to flow into the mixing channel and then into a third chamber to cure;
    positioning the insole into a shoe;
    placing the shoe on a foot; and
    standing in a neutral position as the mixture cures.

14. An insole apparatus comprising:
    a top layer of an insole;
    a shell disposed beneath the top layer of the insole encapsulating a plastic bag including a first and second compartment,
    a first liquid compound contained within said first compartment;
    a second liquid compound contained within said second compartment;
    said first compartment contained within said second compartment
    a mixing channel for mixing the first and second liquid compounds contained within the shell with one end connected to said second compartment of the plastic bag, said end containing a thin breakable membrane, and the mixing channel connected on an opposing end to a mixing bag; and
    the shell having a cavity for accommodating the mixing bag.

15. The apparatus of claim 14 wherein the second compartment is taller than the first compartment so that premix of the first and second compounds occurs in the second compartment before traveling through the mixing channel and into the mixing bag.

* * * * *